(12) United States Patent
Simonson

(10) Patent No.: US 6,916,330 B2
(45) Date of Patent: Jul. 12, 2005

(54) NON CANNULATED DILATORS

(75) Inventor: Robert E. Simonson, Boca Raton, FL (US)

(73) Assignee: DePuy Spine, Inc., Raynham, MA (US)

( * ) Notice: Subject to any disclaimer, the term of this patent is extended or adjusted under 35 U.S.C. 154(b) by 207 days.

(21) Appl. No.: 10/024,221

(22) Filed: Oct. 30, 2001

(65) Prior Publication Data

US 2003/0083689 A1 May 1, 2003

(51) Int. Cl.$^7$ ............................................. A61M 29/00
(52) U.S. Cl. ...................................................... 606/191
(58) Field of Search ........................... 604/161, 164.05, 604/264, 165.01; 606/184, 185, 191, 198

(56) References Cited

U.S. PATENT DOCUMENTS

| | | | |
|---|---|---|---|
| 4,862,891 A | 9/1989 | Smith | |
| 4,863,423 A | 9/1989 | Wallace | |
| 5,106,376 A | 4/1992 | Mononen et al. | |
| 5,158,543 A | 10/1992 | Lazarus | |
| 5,171,279 A | 12/1992 | Mathews | |
| 5,279,567 A | 1/1994 | Ciaglia | |
| 5,431,639 A | 7/1995 | Shaw | |
| 5,472,426 A | * 12/1995 | Bonati et al. | ............... 604/164 |
| 5,489,274 A | 2/1996 | Chu et al. | |
| 5,569,248 A | 10/1996 | Mathews | |
| 5,611,778 A | 3/1997 | Brinon | |
| 5,728,097 A | 3/1998 | Mathews | |
| 5,792,044 A | 8/1998 | Foley et al. | |
| 5,954,635 A | 9/1999 | Foley et al. | |
| 6,010,520 A | * 1/2000 | Pattison | ...................... 606/191 |
| 6,033,406 A | 3/2000 | Mathews | |
| 6,159,179 A | 12/2000 | Simonson | |
| 6,162,170 A | 12/2000 | Foley et al. | |
| 6,162,236 A | * 12/2000 | Osada | ......................... 606/185 |
| 6,206,822 B1 | 3/2001 | Foley et al. | |
| 6,217,509 B1 | 4/2001 | Foley et al. | |
| 6,793,656 B1 | 9/2004 | Mathews | |

* cited by examiner

*Primary Examiner*—Kevin T. Truong
(74) *Attorney, Agent, or Firm*—Nutter, McClennen & Fish, LLP

(57) ABSTRACT

A non-cannulated dilator that is designed with a rigid elongated solid body and with a judiciously configured tip is utilized as the first dilator of a series of dilators which are inserted into the body of a patient for minimally invasive spinal surgery and is made from a solid elongated body, that could be round, ovoid or other cross sectional configuration whose diameter is greater than one and a half (1½) millimeter, and that includes a tool engaging end portion at the proximal end is sufficiently rigid so as not to bend and has a pointed shaped insertion end portion at the distal end with the point of the pointed end being discreetly blunted and utilized in a surgical procedure as a replacement of the typical guide wire and is characterized as providing a "feel" to the surgeon as it penetrates through the tissue and muscle of the patient as it proceeds toward the target.

4 Claims, 3 Drawing Sheets

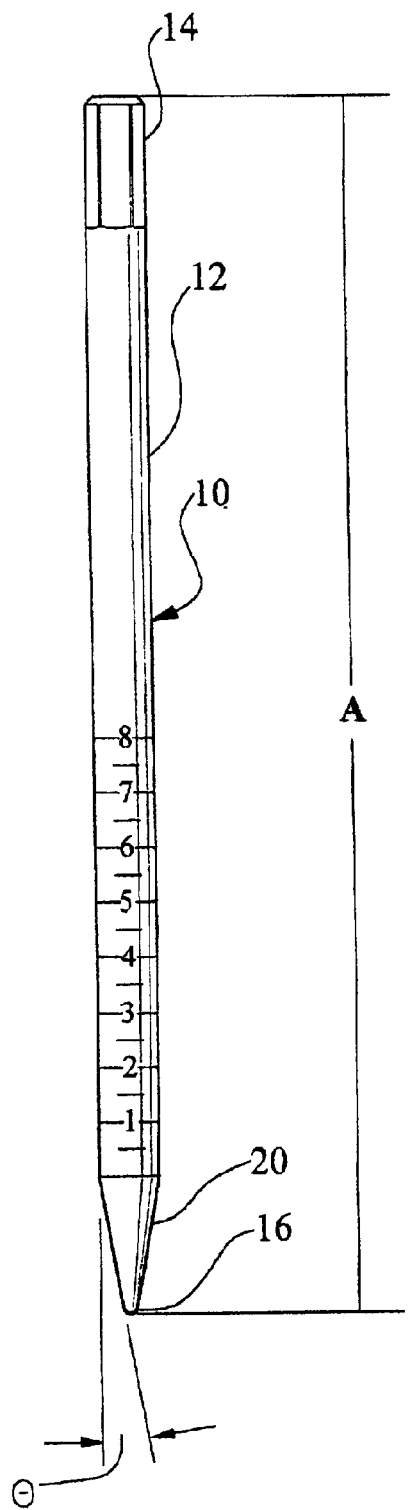
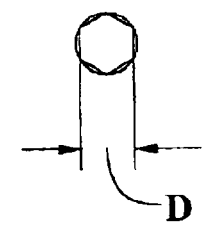
FIG. 4
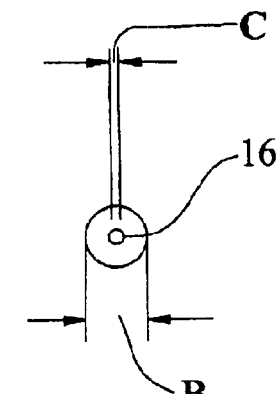
FIG. 5
FIG. 3

US 6,916,330 B2

NON CANNULATED DILATORS

TECHNICAL FIELD

This invention relates to dilation systems and apparatus used in performing minimal invasive surgery and particularly in an application of the instrument in initiating the surgery where dilators are utilized to enlarge the area where the surgery will be performed on a patient.

CROSS REFERENCES

This invention relates to a patent application filed on even date by the applicant of this patent application and entitled "CONFIGURED AND SIZED CANNULA" and bearing Attorney Docket No. N908.

BACKGROUND OF THE INVENTION

As is well known by those skilled in this technology minimally invasive approaches for performing spinal surgery such as laminotomy, medial facetectomy, foraminotomy, nerve root retraction, discectomy and the like, require an initial cut into the skin and tissue of the patient before a series of increasingly larger diameter dilators are inserted to widen the area where the surgery will be performed. As is well known and as described in U.S. Pat. No. 6,159,179 granted on Dec. 12, 2000 to the inventor of this patent application and entitled "Cannula and Sizing and Insertion Method", a guide wire with a sharpened tip to purcutaneously pass through the muscle and engage a target of bone or vertebral disc is typically used. The first dilator is then passed over the guide wire and down to the target. Unfortunately, this method is fraught with a potential danger to the patient. Because the guide wire is relatively thin where it is able to pass through the muscle and ligamentous anatomy, it can protrude into the spinal canal and hence, cause injury to the delicate neural anatomy. If the misplaced guide wire is not detected before the dilators are inserted, catastrophic injury, such as permanent disablement of the patient can occur. Obviously, since this is a potential problem as it is considered a risk to a candidate needing minimally invasive surgery, the use of this type of surgery has been stifled and its potential to grow which ultimately is for the benefit of all patients requiring this type of surgery is thwarted. Of course, the surgical target does not involve the neural anatomy in every spinal surgery and hence, in these situations the use of a guide wire is not a potential hazard and can be safely used.

I have found that I can obviate the problems noted in the above-paragraphs particularly in minimally invasive spinal surgery where it is necessary to access and decompress the spinal nerves and where safety is of a major concern. This invention utilizes a series of muscle dilators in which the first dilator is solid with a design that permits accurate passage through the muscle tissue without the assistance and risk of a pre-placed guide wire. The tip of this inventive dilator is judiciously designed to part and pass through the muscle fibers and allows the surgeon to maintain a course directed toward the intended anatomical target. Because of the inventive dilator when the muscle is passed in the insertion procedure the likelihood for the surgeon forcing the inventive dilator through the ligamentum flavum and continue to pass into the spinal canal is avoided. My invention contemplates dimensioning the non cannulated dilator such that the surgeon when performing the procedure will get a "feel" as the instrument passes through the tissue and muscle of the patient so that the surgeon will have a good sense of what portion of the anatomy is being penetrated. This will help in assisting the surgeon in avoiding the spinal canal.

SUMMARY OF THE INVENTION

This invention relates to an improvement in the instrument utilized in minimal invasive surgery of the type that utilize dilators.

A feature of this invention is a non-cannulated dilator that is made from a solid elongated body having a tip portion at the distal end and a tool engaging portion at the proximal end. The outed diameter dimension of the non-cannulated dilator is critical in that the diameter is sufficiently large so that the instrument is stiff and rigid and greater than one (1½) mm and that the tip is discreetly blunted or rounded.

The foregoing and other features of the present invention will become more apparent from the following description and accompanying drawings.

BRIEF DESCRIPTION OF THE DRAWINGS

These figures merely serve to further clarify and illustrate the present invention and are not intended to limit the scope thereof.

FIG. 3 is an elevated view of the non-cannulated dilator showing the details of this invention;

FIG. 4 is an end view of the proximal end of this invention illustrating the tool engaging portion; and FIG. 5 is an end view of the distal end of this invention illustrating the blunted tip.

DETAILED DESCRIPTION OF THE INVENTION

Figure 1:
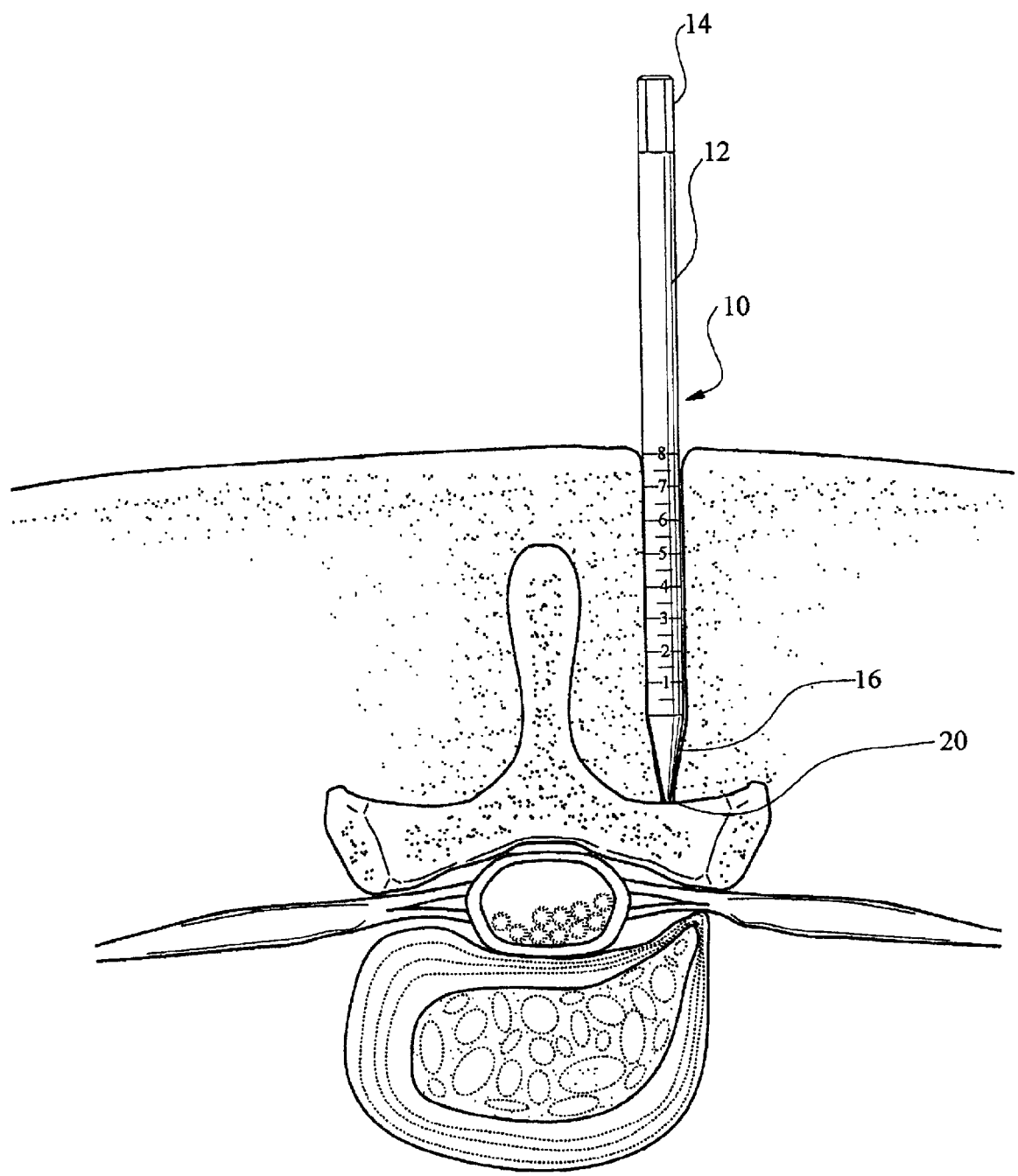
FIG. 1 is a cut-away view of the anatomy of a patient with the inventive non-cannulated dilator inserted into the patient to the target area.
Figure 2:
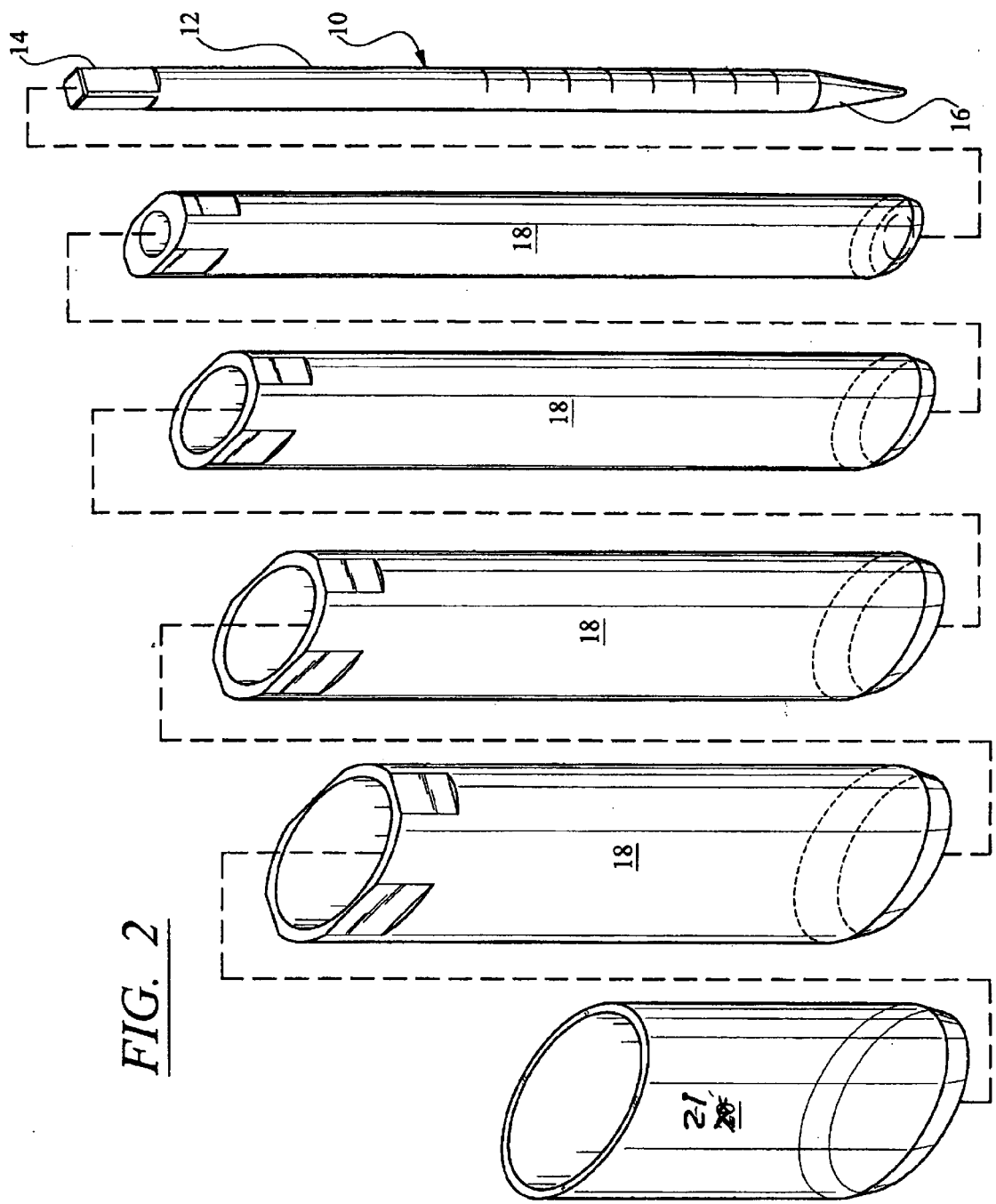
FIG. 2 is a perspective view of a series of sequentially enlarged diameter dilators that are inserted over the non-cannulated dilator in order to widen the cavity to insert the cannula.

While this invention in its preferred embodiment discloses ovoid shaped dilators, it is to be understood as those skilled in this art will appreciate, any shaped dilators and cannulas can be utilized with this invention. However, the initial dilator is non-cannulated, i.e. it is a solid elongated cylindrical body with a judiciously shaped pointed tip at the distal end and a tool receiving tip at the proximal end. Obviously, it is not imperative that the non cannulated dilator be cylindrical or circular in cross section as ovoid or other cross sectional shapes can be substituted therefor without departing from the scope of this invention. The term "cavity" as used herein refers to the opening in the patient formed by the non cannulated dilator, dilators and dilator retractor and becomes a working channel when the non cannula dilator and dilators are removed from the dilator retractor for the surgeon to use to perform the minimal invasive surgery the terms "cannula" and "dilator retractor" as used herein have the same meaning and are used interchangeably.

The invention can best be seen by referring to all the Figs where the inventive non-cannulated dilator is generally illustrated by reference numeral 10 consisting of a cylindrical solid elongated body 12, a tool receiving portion 14 at the proximal end, and the pointed parting tip portion 16 at the distal end. In accordance with this invention the diameter of the cylindrical solid elongated body 12 is greater than one and a half (1½) mm and preferably substantially equal to five (5) mm. The very end of the tip portion 16 is rounded and defines a blunt portion 20 as opposed to a needle type shape that would be found, for example, on the heretofore utilized guide wire. The preferred dimensions are shown in FIGS. 3, 4 and 5. As follows:

A=171.5 (millimeters) (6.750 inches)

θ=16 degrees

B=5.28 mm (0.208") diameter

C=1.0 mm (0.039") diameter

D=Hex shape and extends 1.27 mm (0.50") axially

While these dimensions are disclosed in the preferred embodiment as being preferred, as one skilled in this art will recognize that these dimensions can be slightly modified without departing from the scope of this invention. However, it is abundantly important that the very tip 20 of the tip portion 16 be blunted and the diameter of the cylindrical body 12 be sufficiently large so that the tissue and muscle of the area being penetrated affords a resistance whereby the surgeon will have a feel as the instrument penetrates different portion of the anatomy. In comparison with a guide wire as used heretofore, the non-cannulated dilator 10 of this invention is relatively rigid and will not bend or flex when attempted to be bent under the normal force of the human hands as opposed to the guide wire that will bend and flex under the same force conditions.

After a small stab wound is made at the entry point, as shown in FIG. 1, the non cannulated dilator 10 is "worked" by forcing and partially rotating the dilator with the use of a tool (not shown) attached to the tool engaging end 14 until it reaches its target, and in this instance, until it reaches the inferior edge of the superior lamina. Obviously, under circumstances where the tissue and muscle do not pose a restrictive force that is sufficient to justify the use of a tool when being inserted, the non cannulated dilator may be inserted without the use of a tool. As is apparent from FIG. 1, the tip portion 16 is designed to pass through the muscle fibers and allows the surgeon to maintain a course directed toward the intended anatomical target.

Once the target has been reached, each of the dilators 18 are sequentially inserted over the non cannulated dilator in the order of the smallest to the largest diameter dilator and likewise are worked with the use of a tool until the target is reached. The non cannulated dilator 10 can be marked with a graduated scale that the surgeon can use to select the proper sized dilator retractor or cannular 21. The cannula or dilator retractor 21 is inserted over the last of the dilators 18 whereby the surgeon then has access to the target in order to proceed with the surgery or stated another way the dilator retractor 21 defines a working channel to accommodate all of the instruments used in the surgical procedure.

Obviously, in the procedure for obtaining the working channel enumerated in the immediately above paragraph, the inventive non-cannulated dilator 10 replaces the heretofore utilized guide wire avoiding or at least avoiding the likelihood of passing through the ligamentum flavum and into the spinal canal.

Although this invention has been shown and described with respect to detailed embodiments thereof, it will be appreciated and understood by those skilled in the art that various changes in form and detail thereof may be made without departing from the spirit and scope of the claimed invention.

I claim:

1. In combination, a plurality of dilators and a non cannulated dilator, for use in performing minimal invasive surgery, each of said plurality of dilators having a straight through bore and dimensioned to complement the preceding dilator of said plurality of dilators for fitting over the next preceding dilator of said plurality of dilators for insertion into an access hole formed in a patient for parting the tissue adjacent to the access hole so as to enlarge the surgical plane, said non cannulated dilator having an elongated solid body configured to fit into the straight through bore of the dilator of said plurality of dilators with the smallest diameter of the straight through bore, said elongated solid body being rigid and the diameter of said elongated solid body being greater than one and a half millimeters, and said elongated solid body includes indicia indicative of a graduated scale whereby the depth of the insertion is measured.

2. A non cannulated dilator as claimed in claim 1 wherein the diameter of said solid body is substantially equal to five millimeters.

3. A non cannulated dilator as claimed in claim 1 including a tool portion at the proximal end of said elongated solid body.

4. A non cannulated dilator as claimed in claim 3 wherein said elongated solid body is cylindrical in shape.

* * * * *